United States Patent
Gupta et al.

[11] Patent Number: 5,866,075
[45] Date of Patent: Feb. 2, 1999

[54] DEVICE USEFUL FOR SENSING AMMONIA AND NITROGEN OXIDES(S) GASES AT ROOM TEMPERATURE

[75] Inventors: Ram Pratap Gupta; Purushottam Das Vyas, both of Pilani, India; Zenko Gergintschew, Munich; Dagmar Schipanski, Ilmenau, both of Germany

[73] Assignee: Council of Scientific and Industrial Research

[21] Appl. No.: 998,654

[22] Filed: Dec. 29, 1997

[51] Int. Cl.⁶ ................................... G01N 27/00
[52] U.S. Cl. .................. 422/88; 73/23.31; 73/31.05; 73/31.06; 73/31.07; 204/425; 204/426; 204/428; 204/429; 422/83; 422/94; 422/96; 422/97; 422/98; 436/111; 436/113; 436/116; 436/117; 436/118; 436/149; 436/151; 436/153
[58] Field of Search ................ 73/23.31, 31.05, 73/31.06, 31.07; 204/425, 426, 428, 429; 422/83, 88, 94, 96, 97, 98; 436/111, 113, 116, 117, 118, 149, 151, 153

[56] References Cited

U.S. PATENT DOCUMENTS

| | | | |
|---|---|---|---|
| 3,673,069 | 6/1972 | Niedrach et al. | 204/195 G |
| 4,347,114 | 8/1982 | Kimura et al. | 204/195 S |
| 4,478,704 | 10/1984 | Miyoshi et al. | 204/412 |
| 4,586,143 | 4/1986 | Kaneyasu et al. | 364/509 |
| 5,071,626 | 12/1991 | Tuller | 422/98 |
| 5,362,651 | 11/1994 | Soltis et al. | 436/134 |

FOREIGN PATENT DOCUMENTS

| | | |
|---|---|---|
| 0632265 | 1/1995 | European Pat. Off. . |
| 2479471 | 10/1981 | France . |
| 5332972 | 12/1993 | Japan . |

OTHER PUBLICATIONS

Halasz et al Decomposition of nitric oxide and its reduction by co over super–conducting and related cuprate catalysts. Catalysis Letters 11 (1991) 327–334.

Mizono et al "Reaction between Nitrogen Monoxide and Carbon Monoxide over Super–conducting Bi Sr CeCu and Related Mixed Oxides", 1991 Bull. Chem. Soc.Jpn 64 1383–1385.

Grantscharore et al "Gas Sensing Characteristics of Super-Conducting Coprates," Chemistry Letters, 1991, pp. 1759–1762.

Huang et al "High Tc Superconductors as Nox and $Co_x$ sensor materials". Solid State Ionics 57 (1992) 7–10.

*Primary Examiner*—Jill Warden
*Assistant Examiner*—Sharidan Carrillo
*Attorney, Agent, or Firm*—Dickinson Wright, PLLC

[57] ABSTRACT

A device for sensing ammonia ($NH_3$) and nitrogen oxide ($NO_x$) gases comprising: a sensor for detecting said ammonia and said nitrogen oxide gases, said sensor including a substrate and a layer consisting of cuprate material for detection of said ammonia and said nitrogen oxide gases, wherein said layer of cuprate material is selected from the group consisting of Y:Ba:Cu:O (YBCO) and Bi:Sr:Ca:Cu:O (BSCCO); a sensor holder for supporting said sensor; a perforated cap positioned over said sensor, said perforated cap having openings for passage of said ammonia and said nitrogen oxide gases to said sensor; a detection circuit communicating with said sensor for measuring output from said sensor; and a display or recording device connected to said detection circuit for displaying or recording a concentration of said ammonia and said nitrogen oxide gases based on the output from said sensor.

4 Claims, 2 Drawing Sheets

DEVICE USEFUL FOR SENSING AMMONIA AND NITROGEN OXIDES(S) GASES AT ROOM TEMPERATURE

FIELD OF INVENTION

This invention relates to a device useful for sensing ammonia and nitrogen oxide(s) gases at room temperature.

The present invention particularly relates to a device which incorporates a sensor capable of sensing ammonia and nitrogen oxide(s) gases at room temperature.

BACKGROUND OF INVENTION

The extensive pollution problems in modem industrialized societies are adversely affecting our health and environment. Ever increasing industrialisation and number of automobiles make it absolutely necessary to constantly monitor and control air pollution in the environment. In many industries gases have become increasingly important as raw materials. Therefore, it has become very important to develop highly sensitive gas sensors and systems to prevent accidents and air pollution due to gas leakage. As a result, new and powerful research areas have emerged in our battle for awareness and environmental and health monitoring. The research and development of solid state gas sensor is one such area. Such sensors should allow continuous monitoring of the concentration of particular gases in the environment in a quantitative and selective manner.

Solid state gas sensors use an appropriate material, either in bulk form or in thick or thin film form as gas sensing element. The working principle for gas detection of these sensors is based on change in i) work function; ii) resistance iii) dielectric constant and or iv) mass of the sensing element due to adsorption of a gas. The resultant change in any one of these properties is measured to determine the presence and percentage of the gas in the ambient. Most of conventional sensors employ bulk or thick films of a gas sensing material.

However, in recent sensors, thin films are used as modern thin film preparation techniques give better control on gas sensing properties of a material.

Hitherto known gas sensors based on thin films of materials are of three kinds. First, metal oxides such as $SnO_2$, ZnO, $Ga_2O_3$ etc. (Taguchi: UK Patent 1280809, Mosely: Sensors & Actuators, B 6, 1992). Second, catalytic metals like Pd and Pt (I. Lundstrom et. al: Appl. Phys. Letts. 26, 1975, Sh. Kaihatsu: JP 1213563 A) and third, a special class of organic materials such as Phthalozyanine, Polypyrol u. a. (P. M. Burr et.al: Thin-Solid Films, 151, 1987, M. Josowicz: "Organic semiconductors as chemical sensor materials", Habilitation Universitat der Bundeswehr Munchen). The working principle for gas detection of most of these sensors is based on change in work function of the thin films, due to adsorption of a gas which in turn produces electrical signal. This signal is measured for qualitative and quantitative detection of a particular gas under test in the ambient. However, for the first type of sensors i.e. metal oxide based gas sensors, energy is needed for chemo-physical reactions on the sensing layer. This is achieved by heating the sensitive layer. Therefore, operating temperature of metal oxides based sensors is few hundred degree celsius e.g. from 300° C. to 1000° C. Reference may be made to (i) UK Patent 1280809—A. Mandelis (ii) C. Christofides: A Series of monographs on Analytical Chemistry and its Applications, ed. J. D. Winefordner, Vol. 125, John Wiely & Sons, INC. N.Y. 1993, Chapters 1 to 3 & Refs. there in, and (iii) M. Fleischer et. al. Sensor & Actuators B 25–27, 1995. The sensitivity, selectivity and dynamic response of these metal-oxide based sensors are temperature dependent and this necessitates them to operate at elevated temperatures. To realize these sensors, a heater is provided to heat the sensing film. Generally a thin film heater is fabricated on the back side of the sensing film and electrical power is supplied to it to achieve the desired temperature. Additionally, a temperature sensor is also required to be incorporated with the gas sensor to control the power to regulate the temperature of the sensor. Therefore, a heater and a temperature sensor are integral components of a gas sensing system based on metal-oxide sensors. In this way, heating requirement of the sensor makes fabrication technology and design of the sensing system very complex. It also necessitates thermal isolation between the sensor and the measurement circuit. Further, sensitivity of these sensors is critically dependent on film structure and its preparation technique (Peschke, M. et.al, sensors & Actuators B1, 21, 1990, Peschke, Ph. D. Thesis, 1990, Universitat der Bundeswehr Munchen, A. Mendelis and C. Christofides: Ref. above). The high temperature requirement of these sensors precludes their applications to battery operating equipments. Although application of catalytic metals films like Pt and Pd in FET or CCFET (Capacitive controlled FET) gas sensors has demonstrated room temperature operation (I. Lundstrom et. al, Sensors & Actuators Al, 1981 and Gergintschew, Z., Kornetzky, P., Schipanski, D., Patentschrift DE 433875 At.) but such ammonia gas sensors suffer from a drawback of their cross-sensitivity to hydrogen and hydrocarbon based gases. In addition to poor selectivity, metal film sensors also exhibited ageing effects (K. Dohos et.al Sensors & Actuators 4, 1983). Thus, despite of possibility of room temperature operation, these sensors have not yet became popular due to selectivity problem. For some special applications, the organic materials films are highly sensitive and selective but life time of organic film sensors is limited. Additionally organic materials films are not compatible to microelectronic fabrication technologies and therefore, are not suitable for large scale production. In brief, the gas sensors known to date either can operate at elevated temperatures or suffer from selectivity problem.

SUMMARY OF THE INVENTION

The main object of the present invention is to provide a device useful for sensing ammonia and nitrogen oxide(s) gases at room temperature, which obviates the drawbacks of the hitherto known devices for gas sensing applications.

Another object is to provide a device useful for sensing ammonia and nitrogen oxide(s) $NO_x$ gases at room temperature which incorporates a sensor capable of sensing gases at room temperature.

Yet another object is to provide a device useful for sensing ammonia and nitrogen oxide(s) gases at room temperature which is capable of sensing $NH_3$ and $NO_x$ selectively.

Still another object is to provide a device useful for sensing ammonia and nitrogen oxide s) gases at room temperature which is not cross sensitive to hydrogen and hydrocarbon based gases. Another object is to provide a device useful for sensing ammonia and nitrogen oxide(s) gases at room temperature which give fast response to test gases even at room temperature i.e the response times are low at room temperature.

Yet another object is to provide a device useful for sensing ammonia and nitrogen oxide(s) gases at room temperature which has high sensitivity and selectivity at or around room temperature.

Through our sustained research efforts we have found the gas sensing properties of thin films of cuprates, which are commonly known as high temperature superconducting cuprates. We found that these materials are sensitive to ammonia and nitrogen oxide(s) gases at room temperature while their sensitivity to carbon monoxide, carbon-dioxide, hydrogen and hydrocarbon gases is negligibly low. The reaction times are in seconds. The device of the present invention relates to application of materials of cuprate-superconductor family as gas sensing element which can be operated at or around room temperature.

BRIEF DESCRIPTION OF THE DRAWINGS

In FIG. 1, of the drawings accompanying this specification a schematic of the device of the present invention is depicted. The device of the present invention consists of a perforated cap (1), a sensor holder (2), a sensor (3), a detection circuit (4) and a display and/or recording unit (5).

Figure 1:
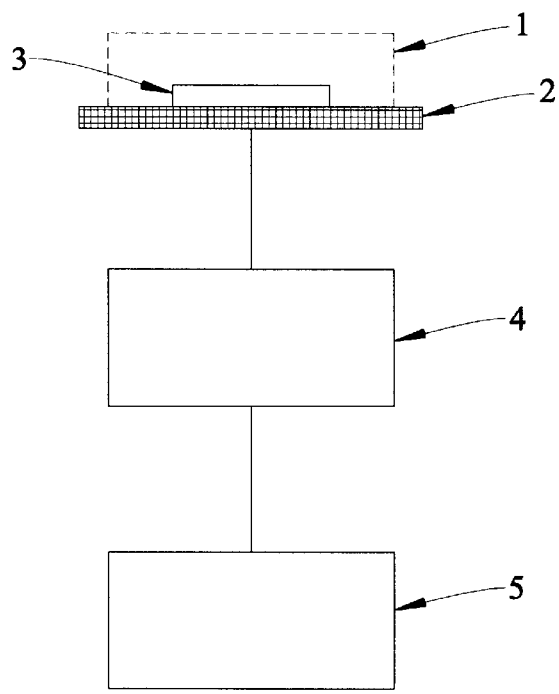
FIG. 1—A sensor device for detection of ammonia and nitrogen oxides.

Accordingly, the present invention provides a device useful for sensing ammonia and nitrogen oxide(s) gases at room temperature, which comprises a sensor holder (2) having a sensor (3), consisting of a layer of material of cuprate family on a substrate, the sensor being provided with a perforated cap (1) resistant to gaseous exposure, the out-put of the said sensor being connected to a known detection circuit (4) coupled to a known display and/or recording unit (5).

In an embodiment of the present invention the sensor may be a layer of material of cuprate family selected from a thin film of metallic or semiconducting Y:Ba:Cu:O (YBCO) or Bi:Sr:Ca:Cu:O (BSCCO) on a substrate selected from magnesium oxide, strontium titnate, gold, silver, stainless steel etc. In another embodiment of the present invention, the sensing layers of the materials can be prepared by any technique known in thin film or microelectronic technologies. In yet another embodiment of the present invention, any compound of cuprate family materials can be used as a sensing layer. In yet another embodiment of the present invention, doping of foreign element/s in a cuprate compound can also be used to prepare sensing layer. In yet another embodiment of the present invention: a thin layer coating of ambient resistant material like gold on the cuprate film can also be used to prepare sensing layer of the sensor.

DETAILED DESCRIPTION OF THE INVENTION

The construction of the device of the present invention is shown in FIG. 1 of the drawings. It consists of a perforated cap (1), which is made of any material which is resistant to hazardous gases to which it is likely to be exposed. For example it can be made of stainless steel or teflon or a special quality plastic. Sensor holder (2) may be such as a standard header generally being used for packaging devices in semiconductor industries. Sensor (3) may be a field effect transistor (FET) or capacitive coupled field effect transistor (CCFET) to which the gas sensing layer is electrically connected. Output of the sensor is connected to any known detection circuit (4) capable of measuring it. The output of the detection circuit is fed to a display or recording unit (5) which contains suitable known circuit/s to display output proportional to the signal output of the sensor.

The working principle of gas sensing is based on change in work function of the sensitive layer due to gas adsorption on its surface. The gas sensitive layer is connected to the gate electrode of a measuring transistor (FET). Therefore, when the sensor is subjected to a gas, it enters into the housing through the holes in the cap and reaches onto the surface of the sensing layer. This gas reacts with the sensitive layer and changes its work function. Since the sensitive layer is electrically connected to the gate of the FET, corresponding change occurs in the gate voltage of the transistor. This change is measured by the detection circuit which further activates the recording or display unit. As change in work function of the sensitive layer is directly proportional to the percentage of the reactive gas present in the gas sample under test, the change in gate voltage and hence output of the detection circuit is a measure of the amount of the reactive gas present in the gas sample.

Gas sensitive films of the cuprates of the present invention can be prepared by sputtering, evaporation, chemical vapor deposition, spin-on, screening or any other film preparation technique known and used in microelectronic technology. Also for preparation of films, any approach known in preparation of commonly known high temperature superconductor can be used. For example a composite material having composition of a cuprate compound and/or separate chemical compounds containing desired elements can also be used to prepare these films. Film deposition can be done on a hot substrate as being done for preparation of in-situ superconducting films or room temperature deposition followed by heating (ex-situ) can also be used. These films may also be semiconducting or metallic in behavior in normal temperature range and can also be covered by a thin protecting film of metal such as gold etc. All these modifications do not change effectively the gas sensing properties of the films of these materials. In brief, the gas sensing properties of the cuprates which have been used as a sensing layer in the present invention are not very critical to composition of the film material or the technique which has been used to prepare the films. The gas sensing property of thin films of cuprates used as a sensing layer in the present invention is based on change in work function of the film material when it is exposed to a gas. The semiconducting films of cuprates are sensitive to ammonia only whereas the metallic films of these materials are sensitive to ammonia and $NO_x$ both As these metallic layers give signal in opposite direction when exposed to $NH_3$ and $NO_x$ respectively, the same sensor can be used to detect ammonia and $NO_x$ selectively. Further, their cross-sensitivity to $H_2$, CO, $CO_2$ and hydrocarbon gases is negligible where as conventional metal or metal oxide sensors are highly cross-sensitive. Therefore, a sensor employing metallic films of cuprates is also highly selective. Morever, these films also exhibit conductivity modulation to high concentrations of the gases and thus can be used to realize conductivity type sensors also. The work function based sensors of these materials shows high sensitivity, even for a few ppm of $NH_3$ in the temperature range of 0° C. to 40° C. The reaction times of the present materials are in seconds while in conventional sensors the response times are several minutes. To improve sensor signal and response times, the metal/metal-oxide sensors are operated at high temperature thus conventional sensors are not suitable for room temperature applications. Therefore, the sensors of the present invention consume low power and suitable for battery operated device/system. Unlike conventional sensors the gas sensing properties of device of the present invention, is not critically or strongly dependent on the technique used for preparation of the sensing films. The room temperature gas sensing capability of the layers of the materials used in the present invention is a novelty.

The following examples are given by way of illustration of the present invention and should not be construed to limit the scope of the present invention:

EXAMPLE 1

Figure 2:
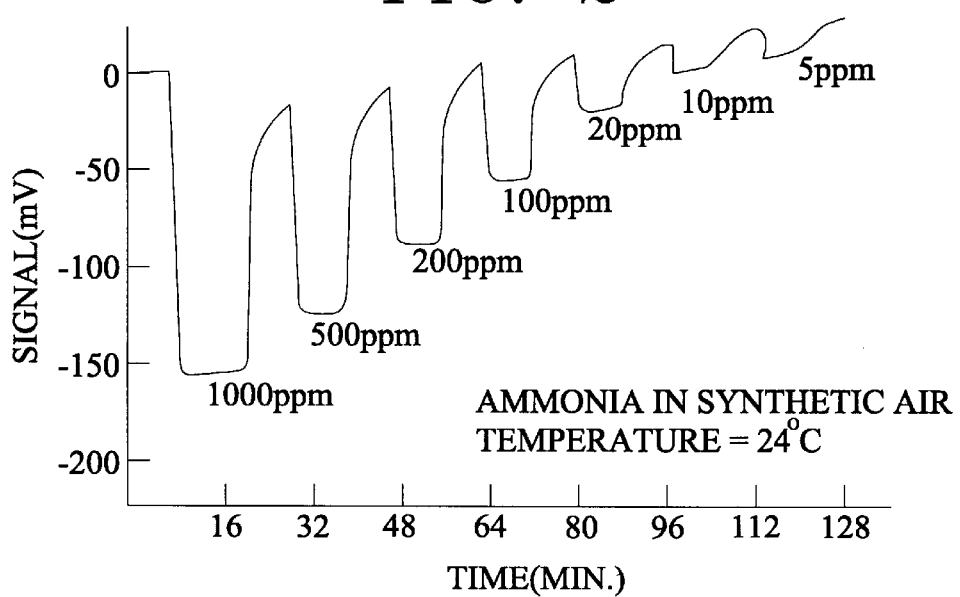
FIG. 2—Detection of ammonia using metallic films of BSCCO materials on MgO/Strontium Oxide.

The device of the present invention was used in a configuration of Capacitively Controlled Field Effect Transistor structure (CCFET). In this structure, sensitive layer forms one electrode of a capacitor and the second electrode of the capacitor is kept floating which is connected to gate of a FET. Due to gas reaction on the sensitive electrode, equal and opposite potential on floating electrode is generated which in turn changes gate voltage of the FET. Change in gate voltage of the FET is recorded as signal produced due to reaction of a gas with the YBCO film. The measured voltage is non-amplified sensor signal and thus it is a direct measure of sensitivity of the film, to the gas to which it is exposed. Different concentrations of test gas in synthetic air is used to measure the sensor signal. We observed that the semiconducting film on silicon-dioxide substrate is highly and selectively sensitive to only ammonia. As seen in FIG. 2, of the drawings accompanying this specification, a signal of more than 10 mV is recorded for 5 ppm of ammonia in air. Typical rise time of 24 seconds and full time of about 250 seconds have been estimated from response of the sensor at 24° C.

EXAMPLE 2

Figure 3:
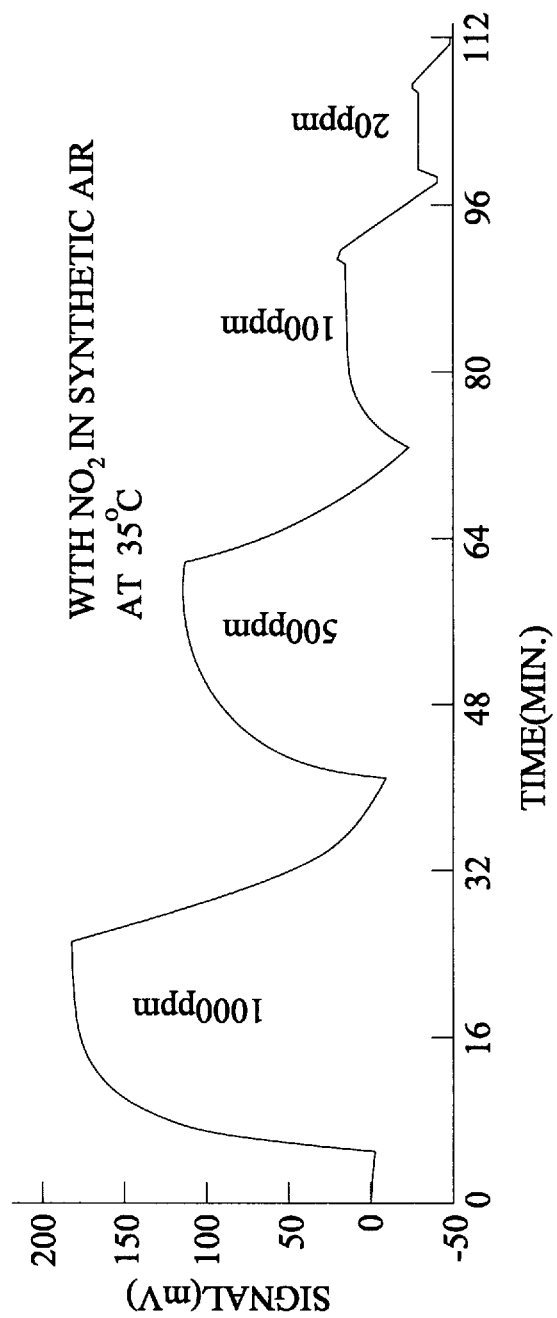
FIG. 3—Detection of nitrogen oxides using metallic films of BSCCO materials on MgO/Strontium Oxide.

The metallic films of BSCCO materials on Mgo/Strontium Oxide are used as a sensing film in the device. For ammonia, response like FIG. 2, of the drawings is recorded. However, for $NO_x$ signal of opposite polarity is observed. FIG. 3, of the drawings shows a typical response of the device when it is exposed to $NO_x$. Response to $NO_x$ is also fast and approximately response times like ammonia are obtained.

EXAMPLE 3

The measurement with our device using YBCO sensing films on MgO/Strontium Oxide, which are metallic in character are also similar to that shown in FIGS. 2 & 3 of the drawings. Thus the response of the device with metallic YBCO films is same as that of the device with BSCCO sensing films. Therefore, the device of the present invention can be used to detect $NH_3$ and $NO_x$ selectively.

EXAMPLE 4

The measurements at different temperatures(5° C., 18° C., 22° C. and 35° C.) illustrate that the response times are not much influenced by operating temperature while sensor signal is reduced to 40% when temperature is increased from 18° C. to 35° C. However, it is decreased only by 5% if the temperature is reduced to 5° C. These results evince that the sensitivity of YBCO to ammonia is optimal in the temperature range of 15° C. to 25° C.

EXAMPLE 5

The measurements with gases like hydrogen, propane, methane, ethane, carbon mono-oxide, carbon dioxide and nitrous oxide gases indicate that either the sensor signal is negligibly low or it does not behave like a sensor.

EXAMPLE 6

We have coated the cuprates films with a thin layer of gold and investigated the sensor response to gases. We found that sensing behaviour of the gold coated film is same as that of the bare films. This evince that cuprates film can be coated with a thin protecting layer without affecting the sensor performance.

From example 1, we observe that semiconducting cuprates are highly sensitive to ammonia only. Examples 2 and 3 evince that metallic cuprates are sensitive to both ammonia and $NO_x$. Since out put signal voltage of the sensor is of opposite polarity in these two cases the same sensor can be used selectively to detect $NH_3$ or $NO_x$ at room temperature. The example 4, suggests that the device of the present invention is useful for sensing gases at and around room temperature The example 5, demonstrates that the present device does not show cross-sensitivity to hydrogen or hydrocarbon gases thus it is suitable for sensing ammonia and $NO_x$ selectively. Further, the example 6, suggests that gold coated sensing films are also suitable for the sensing device.

The main advantages of the device of the present invention are:

1. The device is capable of sensing gases at or about room temperature.
2. A film of any compound of family of materials known as cuprates particularly metallic or semiconducting cuprates can be used as a sensing layer to construct sensor of the device which can be operated at or around room temperature.
3. The device is useful for sensing ammonia and $NO_x$ with high sensitivity and selectivity without cross-sensitivity to hydrogen and hydrocarbon based gases.
4. The device is capable of sensing both ammonia and $NO_x$ selectively as sensor output signal is of opposite polarity in detection of these two gases.
5. Gas sensing capability of the device at room temperature eliminates requirement of heater and temperature sensor which are otherwise essential in a conventional sensor.
6. The power consumption required to heat the sensing layer is completely eliminated in the present device.
7. Battery operation is possible in the present case.
8. The capability of room temperature gas sensing makes it viable to fabricate sensing layer on the same semiconductor chip on which detection and measurement circuits are fabricated.
9. The film preparation techniques to prepare sensing layers of cuprates used in the present device are compatible to micro electronic technology.

We claim:

1. A device for sensing ammonia ($NH_3$) and nitrogen oxide ($NO_x$) gases at room temperature comprising:

a) a sensor for detecting said ammonia and said nitrogen oxide gases, said sensor including a substrate and a layer consisting of cuprate material for detection of said ammonia and said nitrogen oxide gases;

b) a sensor holder for supporting said sensor;

c) a perforated cap positioned over said sensor, said perforated cap having openings for passage of said ammonia and said nitrogen oxide gases to said sensor;

d) a detection circuit communicating with said sensor for measuring output from said sensor in response to exposure of said sensor to said ammonia and said nitrogen oxide gases; and e) a display or recording device connected to said detection circuit for displaying or recording a concentration of said ammonia and said nitrogen oxide gases based on said output from said sensor.

2. The device of claim 1, wherein the layer of cuprate material is selected from the group consisting of Y:Ba:Cu:O (YBCO) and Bi:Sr:Ca:Cu:O (BSCCO) and the substrate is selected from the group consisting of magnesium oxide, strontium oxide, silver, gold, and stainless steel.

3. The device of claim 1, wherein the layer of cuprate material is provided with a protective coating selected from the group consisting of gold, platinum, and silver.

4. The device of claim 2, wherein the layer of cuprate material is provided with a protective coating selected from the group consisting of gold, platinum, and silver.

* * * * *

UNITED STATES PATENT AND TRADEMARK OFFICE
CERTIFICATE OF CORRECTION

PATENT NO. : 5,866,075
DATED : February 2, 1999
INVENTOR(S) : Gupta et al.

It is certified that error appears in the above-identified patent and that said Letters Patent is hereby corrected as shown below:

Insert Technical University of Ilemnau as an Assignee.

Signed and Sealed this

First Day of May, 2001

Attest:

NICHOLAS P. GODICI

Attesting Officer      Acting Director of the United States Patent and Trademark Office